United States Patent [19]
Weber et al.

[11] Patent Number: 5,613,977
[45] Date of Patent: Mar. 25, 1997

[54] GRIPPING AND/OR CUTTING INSTRUMENT FOR ENDOSCOPIC PURPOSES

[75] Inventors: Robert Weber, Chino Hills; Georg Schaber, Venice, both of Calif.; Lars Frings, Remscheid, Germany

[73] Assignee: Friatec AG Keramik-und-Kunstoffwerke, Mannheim, Germany

[21] Appl. No.: 442,767

[22] Filed: May 17, 1995

Related U.S. Application Data

[63] Continuation of Ser. No. 94,615, Jul. 20, 1993, abandoned.

[30] Foreign Application Priority Data

Jul. 22, 1992 [DE] Germany ............... 42 242 26.6
Oct. 16, 1992 [DE] Germany ............... 42 350 23.9

[51] Int. Cl.⁶ ............... A61B 17/28; A61B 17/32
[52] U.S. Cl. ............... 606/170; 606/205; 606/207; 606/208
[58] Field of Search ............... 128/751, 752; 606/205–208, 170, 174; 81/416

[56] References Cited

U.S. PATENT DOCUMENTS

| | | | |
|---|---|---|---|
| D. 274,096 | 5/1984 | Shutt . | |
| 3,515,139 | 6/1970 | Mallina | 606/207 |
| 3,585,985 | 6/1971 | Gould | 606/208 X |
| 3,814,102 | 6/1974 | Thal | 606/207 |
| 4,201,213 | 5/1980 | Townsend | 606/174 |
| 4,369,788 | 1/1983 | Goald | 606/207 |
| 4,478,532 | 10/1984 | Puro | 81/416 X |
| 4,569,131 | 2/1986 | Falk et al. | 128/751 |
| 4,674,501 | 6/1987 | Greenberg | 606/174 |
| 4,785,825 | 11/1988 | Romaniuk et al. | 128/751 |
| 4,890,615 | 1/1990 | Caspari et al. . | |
| 4,896,661 | 1/1990 | Bogert et al. | 606/208 X |
| 4,919,152 | 4/1990 | Ger | 128/898 |
| 4,950,273 | 8/1990 | Briggs | 606/205 X |
| 5,219,357 | 6/1993 | Honkanen et al. | 606/205 |
| 5,366,477 | 11/1994 | LeMarie et al. | 606/208 |
| 5,489,292 | 2/1996 | Tovey et al. | 606/207 |

FOREIGN PATENT DOCUMENTS

| | | | |
|---|---|---|---|
| 356185 | 7/1922 | Germany | 606/205 |
| 827927 | 12/1951 | Germany . | |
| 2119696 | 11/1983 | United Kingdom | 606/208 |

*Primary Examiner*—Michael H. Thaler
*Attorney, Agent, or Firm*—Hill, Steadman & Simpson

[57] ABSTRACT

A gripping and/or cutting instrument for endoscopic purposes, comprising two limbs that are pivotable relative to one another around an axis and that each respectively comprise a lug for fingers of a user, one of the limbs being hinged to a proximal end of a transmission rod, and having a support shoulder for a finger of the user at the lug of this limb. Two blades are provided movable relative to one another between an open position and a closed position, one thereof being hinged such to a distal end of the transmission rod that the closed position is achieved by applying a pressure onto the transmission rod, whereas the opened position is achieved by applying a pulling force onto the transmission rod, and in that the support shoulder is curved in the direction toward the second limb.

19 Claims, 8 Drawing Sheets

GRIPPING AND/OR CUTTING INSTRUMENT FOR ENDOSCOPIC PURPOSES

This is a continuation of application Ser. No. 08/094,615, filed Jul. 20, 1993, now abandoned.

BACKGROUND OF THE INVENTION

The invention relates to a gripping and/or cutting instrument for endoscopic purposes having two limbs, which are pivotable toward one another around an axis and each of which respectively comprises a lug for the fingers of a user, one of the limbs being articulated to a proximal end of a transmission rod and having a support shoulder for a finger of the user on the lug of said limb.

Endoscopic instruments intended to simplify operative treatment on tissue or vessel lesions are known in a large number of variants, particularly when designed as a gripping or cutting instrument. Thus, U.S. Design Pat. No. 274,096 shows an arthroscopic cutting instrument, whose gripping limbs can be opened and closed with the aid of a mechanism operable via the members.

Another instrument of the aforementioned type is known from U.S. Pat. No. 4,890,615. Said instrument is more particularly intended to form sutures within the human body. For this purpose the tissue is clamped between jaws movable relative to one another, whereof one is constructed as a hollow needle through which the suture thread is drawn. The jaws can be opened and closed by a mechanism operable by means of the limbs, a tension being applied to the transmission rod when the jaws are to be closed. The support shoulder provided on the lug of one of the limbs serves as a support for a finger and consequently assists the closing movement of the jaws.

SUMMARY OF THE INVENTION

The object of the present invention is to provide an instrument for endoscopic purposes, particularly a gripping and cutting instrument, which can be precisely guided and with which extremely clean cuts in which the surrounding tissue is not injured are made possible.

This object is achieved by a gripping and/or cutting instrument of the afore-mentioned type having two closable blades that can be moved relative to one another between an open position and a closed position, one of the blades being hinged to a distal end of a transmission rod such that the open position is achieved upon exertion of a tension onto the transmission rod, and the closed position is achieved upon exertion of a compression force onto the transmission rod. A support shoulder extending from one of the limbs is curved in the direction toward the second limb.

Advantageous developments include hinging the transmission rod to a bearing element that is rigidly connected to the respective limb and which is pivotable around the pivot axis between the two limbs, and whose "pivoting" or "swiveling" angle is limited. This bearing element can provide a recess into which a stop pin registers to limit this angle. For ease of operation, the bearing element can provide on opposite sides, a respective disk of friction-reducing material such as polytetrafluorethylene. The closable blades can have serrations arranged on one or both blades or a plurality of arcuate cutting sub-regions adjoining one another that are likewise offset from one another by cutting teeth.

The transmission rod can be accommodated in an elongated tube in which a bush of friction-reducing material such as polytetrafluorethylene essentially surrounds the transmission rod. A lock mechanism can be provided which holds the first limb and the second limb in an adjustable, relative angular position. The lock mechanism can provide a first arm whose end is hinged to one of the limbs and whose other end carries a ratchet means that can be brought into engagement with a second compatibly fashioned ratchet means at the other limb. The ratchet mechanism can be a tooth arrangement. A through opening into which the second ratchet means inserts can be fashioned in the limb holding the second ratchet means, the through opening being dimensioned such that at least the ratchet means at the arm can be conducted through the unobstructed part of the through opening. The second ratchet means can also comprise a tooth arrangement.

The locking mechanism can comprise an actuation lever with which the arm can be pivoted around its point of articulation. The point of articulation can be placed at the first limb. The actuation lever can be curved corresponding to the curvature of the support shoulder. The closable blades can form a gripping device having sections with blunt toothing, whereby these sections are fashioned essentially circular.

According to the invention, blades movable toward one another between an open position and a closed position are provided, whereof one is articulated to a distal end of the transmission rod such that the open position is reached on applying a tension to the transmission rod, whereas the closed position is reached on applying a pressure to the transmission rod and such that the support shoulder is curved in the direction of the second limb. Since the transmission rod reacts to pressure, it is possible to transmit greater forces than hitherto. Using a mechanism operating in this way it is also possible to provide a simple overload protection device, such as a shear pin, which breaks if the forces applied or to be applied exceed a limit value. In addition, the assembly of the instrument according to the invention is greatly simplified because there is no need to provide a precise suspension for a tension member.

As a result of the inventive design of the support shoulder, the relative movement of the limbs can also be controlled during their opening motion. Hitherto known embodiments are endoscopic instruments having a support shoulder which facilitates the closing movement of the limbs. However, for ergonomic and physiological reasons due to the hand muscles designed for a closing movement, the latter can always be performed in a controllable manner, whereas this does not directly apply with respect to the arm opening movement. It is now possible to involve the muscles of another finger of the user in the opening movement.

Advantageously, the transmission rod is articulated to a bearing element that is pivotable around the axis and is rigidly connected to the corresponding limb and whose pivoting angle is limited. Thus, both the opening movement and the closing movement of the blades can be limited to a desired extent.

The limitation of the pivoting angle can be obtained in simple manner when the bearing element has a recess into which the stop pin engages. The recess can be a segment-like recess of the bearing element in the edge region thereof, which offers manufacturing advantages; however, it can also be formed by an optionally curved, elongated hole in the interior of the bearing element.

The handling of the instrument is further simplified when the bearing element is provided on both sides with a disk made from friction-reducing material, such as polytetrafluorethylene. Thus, a complete bearing in friction-reducing material is ensured on both sides of the disk.

According to a particularly advantageous development of the invention, at least one of the blades is serrated. A plurality of adjoining arcuate, sub-cutting areas between the cutting teeth can be provided according to the invention. Tissue to be cut can no longer slip out of the area between the blades at the start of cutting and the once gripped tissue is reliably cut with a uniform exertion of force. The disadvantage of a unitary blade, whereby it is increasingly more difficult to overcome the cutting resistance on continuing the cut due to the reduction of the lever action, is overcome.

Since the entire instrument is expediently encapsulated, the transmission rod should also be housed in an elongated tube, a bush made from friction-reducing material such as polytetrafluorethylene which surrounds the transmission rod being provided therein. Thus, the uniform movement of the transmission rod when travelling along the tube is ensured, which once again facilitates the handling of the instrument.

In another embodiment of the invention, a locking device is provided, which keeps the first limb and the second limb in an adjustable, relative angular position. Therefore the instrument can be used as a grasping forceps, which can be locked in the gripping position, also as a function of the gripped tissue thickness, so that once the tissue is gripped it is firmly held by the instrument itself without the operator having to constantly maintain the gripping position, Advantageously, the locking device has a first arm, whose one end is articulated to one of the limbs and whose other end carries a ratchet means, which can be engaged with a second, congruently constructed ratchet means at the other limb.

Preferably, the ratchet means at the locking device is a toothing; the second ratchet means can also comprise a toothing.

A through opening into which the second ratchet is let in and which is dimensioned such that at least the ratchet means at the arm can be guided through the unimpeded part of the through opening is preferably provided in the limb comprising the second ratchet means.

Advantageously, the locking device has an operating lever with which the arm can be pivoted about its articulation point.

Preferably, the articulation point is placed at the first limb.

When the operating lever has a curvature corresponding to that of the support shoulder, the locking device can be operated with the same finger that also lies at the support shoulder.

The tip of the instrument is advantageously also designed for seizing or gripping in that the gripping devices have portions with blunt teeth, said portions being substantially circularly positioned.

The invention is described in greater detail below by way of example with reference to the attached drawings.

DETAILED DESCRIPTION OF THE PREFERRED EMBODIMENTS

Figure 1:
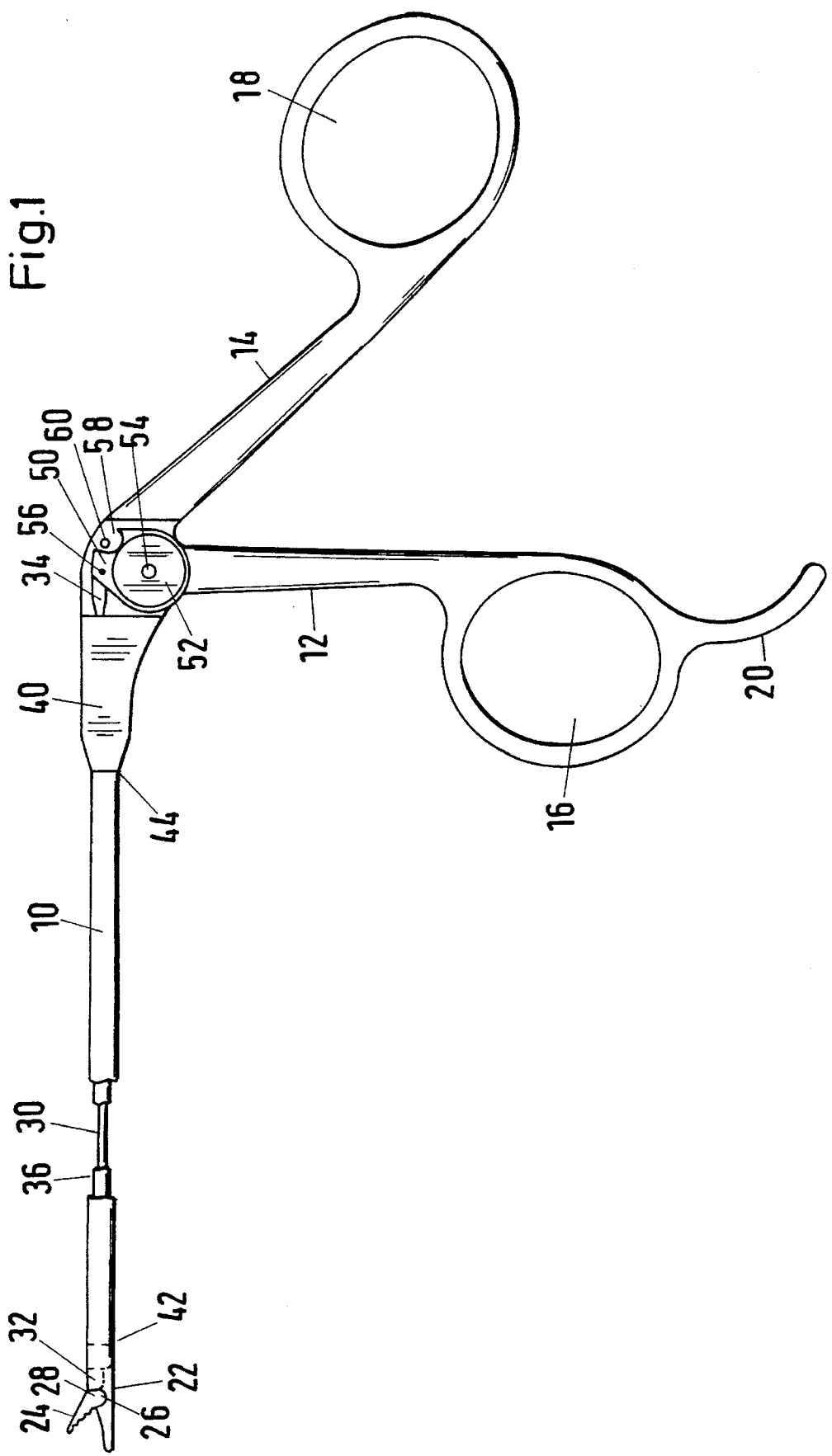
FIG. 1 is an elevational illustration of an instrument of the present invention, partly broken away.

The instrument shown in FIG. 1 is composed of an elongated tube 10 to which the stationary parts of the instrument, namely a fixed blade 22 and a fixed limb 14 are secured at facing ends in a way yet to be set forth. A second, movable limb 12 is provided that is pivotable around an axis 54 and can thus be moved toward the limb 14. The ends of both of the limbs 12, 14 respectively comprise a lug 16, 18, whereby the thumb of a user normally engages into the lug 18 of the stationary limb 14 and the index finger or, potentially, the middle finger of a user normally engages into the lug 16 of the movable limb 12. A support shoulder 20 that is curved in the direction toward the limb 14 is provided at the lug 16, so that a seating surface for another finger of the user derives. This can thus support the opening motion of the limbs 12, 14 relative to one another.

A bearing element 50 through which the axis 52 is essentially centrally guided is provided at that end of the limb 12 lying opposite the lug 16. The bearing element 50 is embedded between two disks of friction-reducing material, only one disk 52 thereof being shown in the figure. For example, polytetrafluorethylene is suitable as material. No particular frictional forces thus have to be overcome when moving the limbs 12, 14 relative to one another and a user is lent a better feeling for the execution of the cutting motion.

A recess or clearance 58, into which a stop pin 60 provided at the limb 14 engages, is provided in the edge region of the bearing element 50. The opening angle or, respectively, the closing angle of the limbs 12, 14 can be set on the basis of suitably selected dimensions of the recess 58; the respectively corresponding angle between two blades 22, 24 can also be set as a result thereof. An excessive opening of the blades is thus prevented and, excessive stressing of a shear pin forming a link pin 56 is also prevented.

A transmission rod 30 is hinged to the bearing element 50, this transmission rod 30 being capable of being moved back and forth in the elongated tube 10. The articulation ensues via a fitting 32 that shall be set forth in greater detail in conjunction with FIG. 7. The entire bearing region is enclosed by a bearing housing 40 which, however, is shown partially cut-away here, whereby the connection of the bearing housing 40 to the elongated tube 10 is undertaken via a welded, soldered or glued connection 44. This connection can also be realized in that an outside thread is applied to the inner tube 10 and a corresponding inside thread is applied to the bearing housing 40, so that the tube parts can be screwed to one another. Securing the connection ensues by adding a special adhesive.

As may be seen in the cut-away section of the elongated tube 10, the transmission rod 30 is surrounded by a bush 36 of friction-reducing material, for example polytetrafluoroethylene once again, so that it can likewise be moved without having to overcome significant frictional resistance. The transmission rod 30 itself is composed of stainless steel.

The stationary blade 22 is fixed with a welded or soldered connection 42 at the distal end of the elongated tube 10, i.e. at that end that lies opposite the bearing element 50. Here, too, a glued connection is possible. The blade 22 has an extremely low profile height of approximately 1 mm, so that a simpler positioning is possible even given firm tissue. The movable blade 24 is pivotable around an axis 26 relative to the blade 22. The transmission rod 30 is also hinged to the movable blade 24 via a lengthening piece 32, whereby the articulation ensues with a pin 28. As a consequence of its shaping with the straight, front terminating edge which merges via a curvature into a lower terminating edge proceeding above the axis 26, the lengthening piece 32 limits the closing of the blades 22, 24 beyond the underside of the blade 22.

FIG. 1 shows the open position of the limbs 12, 14. The stop pin 60 presses nearly against an edge of the recess 58. This open position corresponds to the open position of the blades 22, 24. When the limbs 12, 14 are now closed, then the bearing element 50 together with the recess 58 moves in a counterclockwise direction until the stop pin 60 strikes against the second edge of the recess 58 which lies opposite the first edge. A force of pressure is thereby exerted onto the transmission rod 30 which effects the closing motion of the blades 22, 24, particularly of the movable blade 24.

The axis 54 lies under the axis 56 for the transmission rod 30 in order to force an advancing motion onto the latter for the cutting.

Figure 2:
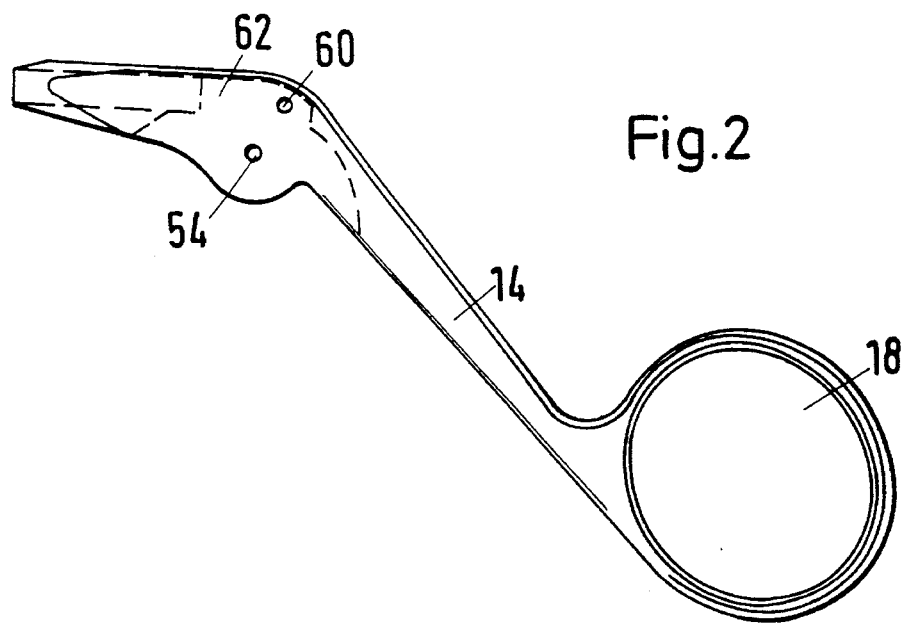
FIG. 2 is an elevational view of a limb of the instrument of FIG. 1, which is intended for the application of a user's thumb.

FIG. 2 shows a detailed illustration of the stationary limb 14. The essentially elliptical lug 18 is applied to one of its ends, fashioned of one piece with the limb 14. A connecting part 62 is arranged at the other end of the limb 14, the stop pin 60 and the pin 54 that forms the axis for the pivoting motion of the two limbs of the instrument relative to one another being arranged on this connecting part 62. The mutual position of the pins 54, 60 is selected such that, in particular, the stop pin 60 can exercise its function in interaction with the bearing element that is not shown in FIG. 2. The connecting part 62 is also formed such that the elongated tube or, respectively, a bearing housing can be fixed thereat.

Figure 3:
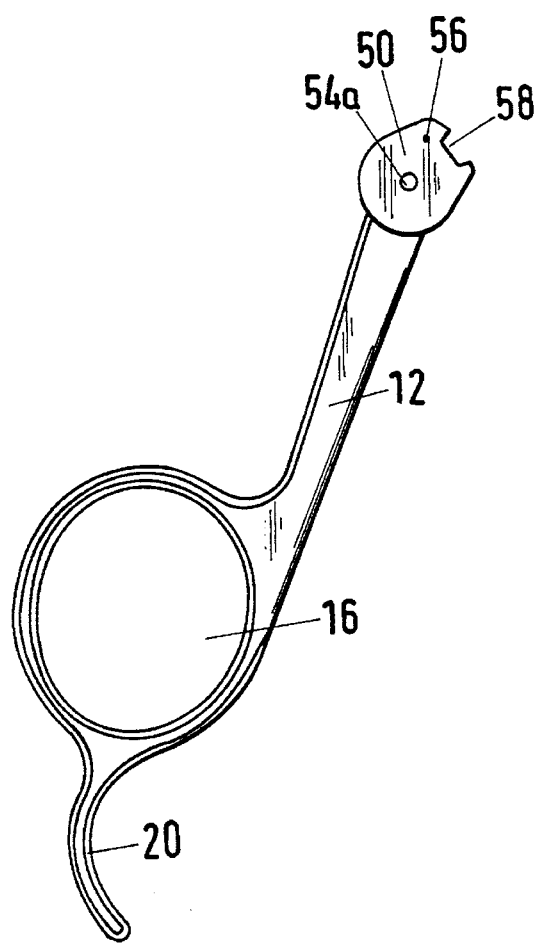
FIG. 3 is an elevational view of a second limb of the instrument of FIG. 1.

FIG. 3 shows a detailed illustration of the movable limb 12. The essentially elliptical lug 16 is again applied to one of its ends. The support shoulder 20 is fashioned at the lug 16 approximately in the extension of the limb 12, the curvature of this support shoulder 20 being selected such that a finger of the user can rest in this curvature at the support stop 20. The bearing element 50 is provided at that end of the limb 12 opposite the lug 16, this bearing element 50 being nearly circularly fashioned and centrally comprising an opening 54a which, with reference to the bearing element 50, defines the swivelling axis for the movement of the two limbs relative to one another. At that side of the bearing element 15 facing away from the limb 12, this bearing element 15 is fashioned somewhat elongated and comprises a recess 58 having the essentially U-shaped section. The point 56 of articulation for the transmission rod is provided adjacent to the recess 58.

Figure 4:
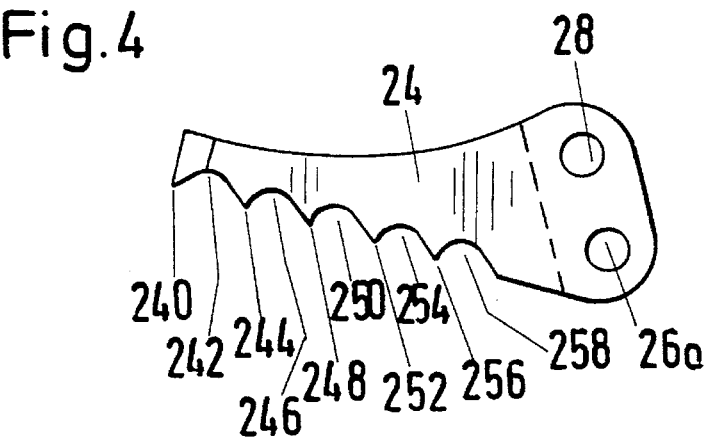
FIG. 4 is an enlarged elevational view of a serrated blade.

In an enlarged view, FIG. 4 shows a side view of the movable blade 24. At its upper region, i.e. at the edge that faces away from the stationary blade, this blade 24 is slightly arcuately curved; the actual cutter region here is composed of five sub-regions 242, 246, 250, 254, 258; in general, four through six sub-regions have proven beneficial, these being respectively separated from one another by cutting teeth 244, 248, 252, 256 that are spaced from one another. The front region of the blade 24 is also fashioned as a tooth 240. Whereas this tooth 240, however, extends essentially perpendicularly relative to the cutting surface of the blade 24, the teeth 244, 248, 252, 256 are directed slightly back, i.e. in the direction toward the axis of the swivel motion of the blades relative to one another. What is thus achieved is that the teeth, beginning with the tooth 256, successively hold the tissue in the region to be cut during the cutting motion, whereas the actual cut is successively implemented in the sub-regions 258, 254, 250, 246, 242. An opening 26a that defines the axis for the swivel motion for the blade 24 as well as the point of articulation for the transmission rod, formed by a pin 28 guided through an opening, is located outside the region of the individual cutters.

Figure 5:
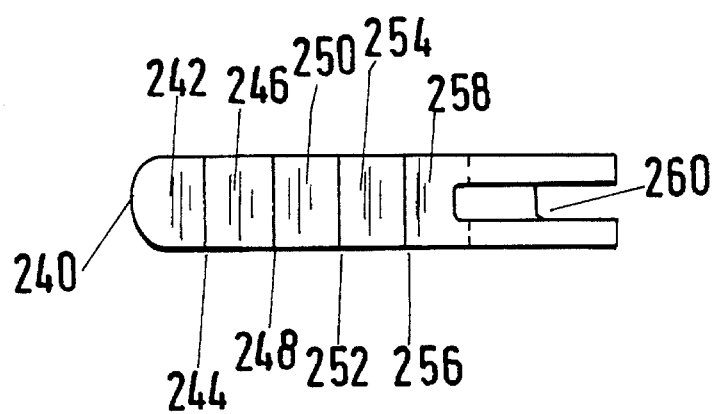
FIG. 5 is a bottom view of the blade of FIG. 4.

What measures are undertaken for fixing the transmission rod may be seen especially clearly in FIG. 5, namely a step-shaped recess 260 on whose step the transmission rod can lie. The front region of the blade that proceeds curved and has the tooth 240 is likewise clearly shown. The teeth 244, 248, 252, 256 extend over the entire width of the blade.

Figure 6:
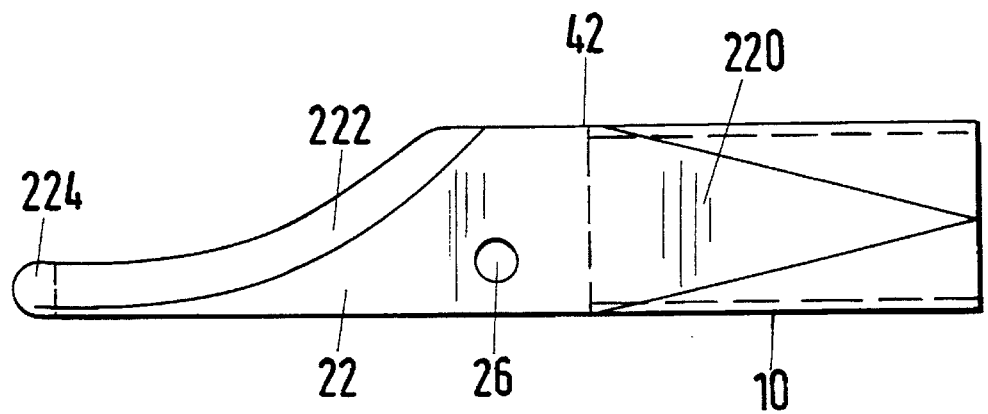
FIG. 6 is an enlarged elevational view of a second, fixed blade of an instrument according to the present invention.

FIG. 6 shows an enlarged view of the stationary blade 22, this comprising a fitting wedge 220 that is designed such that it can be introduced into the elongated tube 10, whereby this is then firmly connected to the blade 22 with a welded, soldered or glued connection 42. The axis 26 for the swivel motion of the blades relative to one another is located preceding the welded, soldered or glued connection 42. A uniform cutting surface 222 which has a curved course and extends over the entire height of the blade 22 and discharges into a rounded-off front 224 is provided at the stationary blade 22.

The blade 22 is quadratic or rectangular in cross section, this promoting stability and also allowing easier assembly.

Figure 7:
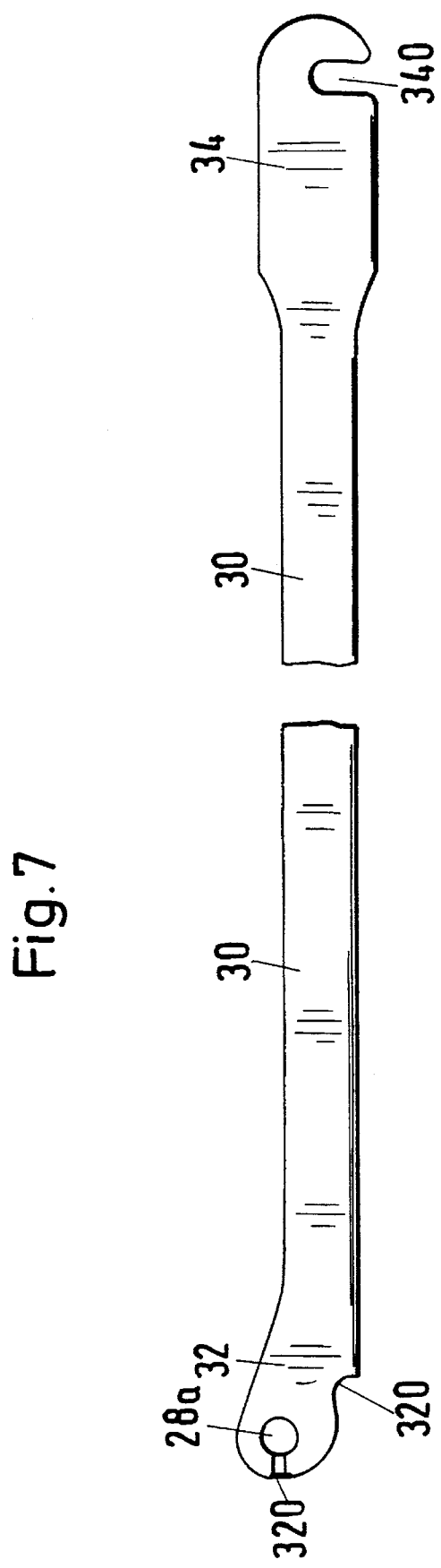
FIG. 7 is an enlarged elevational view of a transmission rod.

FIG. 7 shows an elevational view of the transmission rod 30 in a partially broken view. The ends 32, 34 of an essentially elongated section comprise fittings that respectively move the distal or, respectively, proximal end of the transmission rod 30. A vertical slot 340 that, proceeding from the edge region of the fitting 34, extends in the front region thereof approximately up to the center is provided at the proximal end, i.e. at the fitting 34. This recess is attached in the fashion of a hook to a pin that is provided at the bearing element at the point of articulation of the transmission rod 30, this enabling a simple and fast assembly. An opening 28a through which a pin for the articulation of the transmission rod 30 to the movable blade can be conducted is fashioned at the distal end of the transmission rod 30, i.e., at the fitting 32 that proceeds slightly angled off from the elongated section of the transmission rod 30. A recess 320 which is placed onto the step of the recess shown in FIG. 5 which is described in conjunction with FIG. 5 is located at the lower part.

The weakest part of the instrument is doubtlessly the pin that forms the axis 56. This should be dimensioned as large as possible in order to suppress breakage to the farthest-reaching extent. Due, for example, to the quadratic or, respectively, rectangular fashioning of the blade 22, of the transmission rod 30 and due to the correspondingly designed connections 42, 44, one can anticipate overall that a stable, rugged instrument has been provided.

Figure 8:
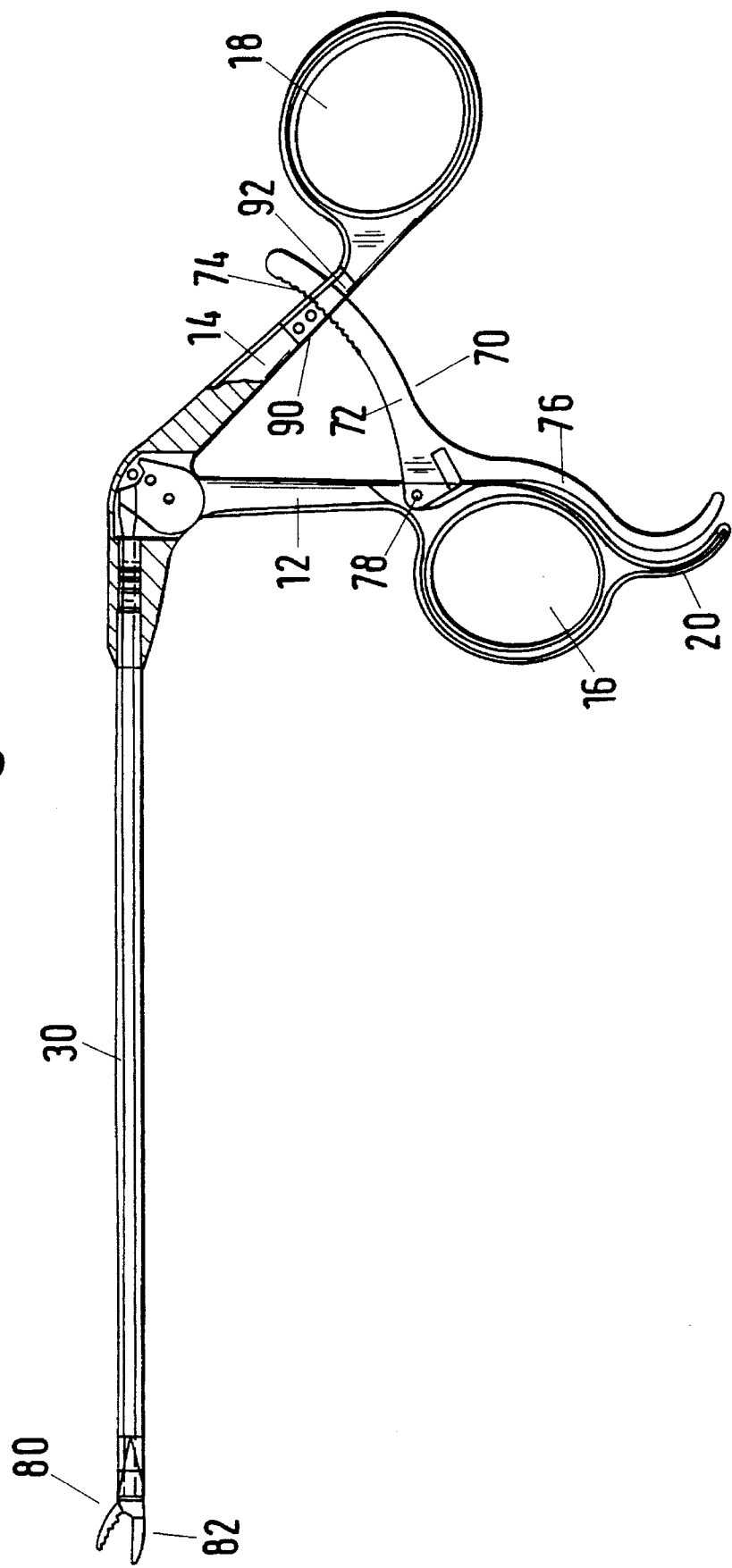
FIG. 8 is a partial sectional view of a second embodiment of the instrument of the present invention as a grasping forceps.

In terms of its closing and opening mechanism, the instrument shown in FIG. 8 corresponds to that of FIG. 1. Since it is to be employed as a gripping or grasping forceps, however, a gripping means 80, 82 that is to be described below in greater detail is provided at the front end of the transmission rod 30. The forceps comprise a lock mechanism 70 with which the limbs 12, 14 can be held in a defined position relative to one another.

The lock mechanism 70 is composed of an arm 72 that is arcuately curved and is dimensioned such that its arc at least sweeps the maximum opening angle of the limbs 12, 14. The arm 12 has one of its ends pivotably attached to the limb 12 at a point 78 of articulation, whereby the pivoting motion is implemented with an actuation lever 76 that is formed corresponding to the curvature of the lug 16 at that side adjoining the limb 12 and corresponding to the curvature of the support shoulder 20. The second end of the arm 72 is conducted through a through opening 92 in the limb 14 in which a ratchet means 90 is also accommodated. Facing toward the arm 72, the latter comprises a toothing that can be brought into engagement with a toothing 74 on the arm 72 via the actuation of the actuation lever 76. The position of the limbs 12, 14 relative to one another is fixed when the toothings are in engagement.

Figure 9:
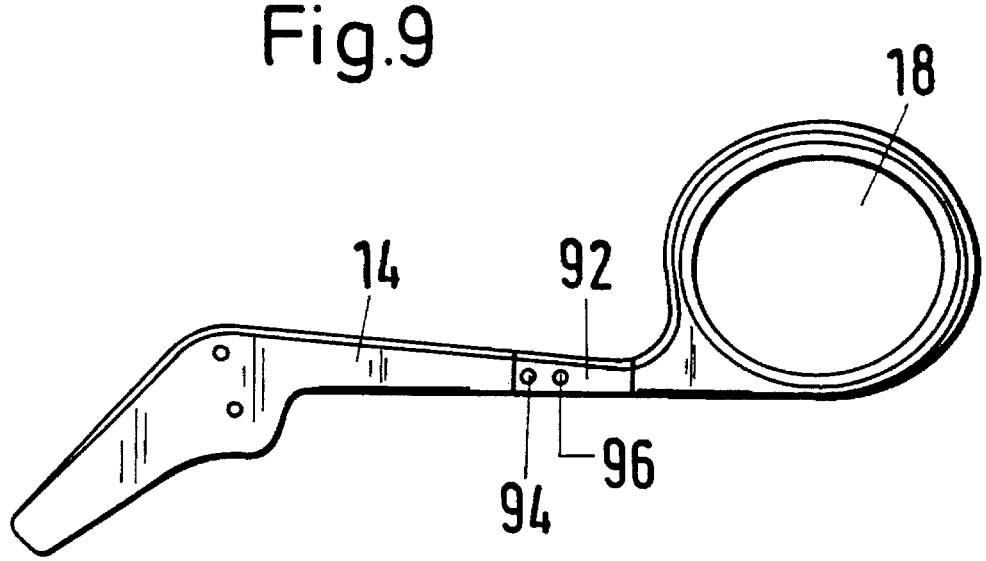
FIG. 9 is an elevational view of a limb of FIG. 8 that is actuated with the user's thumb.

FIG. 9 shows the limb 14 in detail. The through opening 92 is provided in the proximity of the lug 18. The ratchet means is fixed therein by pins or the like that are provided by bores 94, 96 in the walls that limit the through opening 92.

Figure 10:
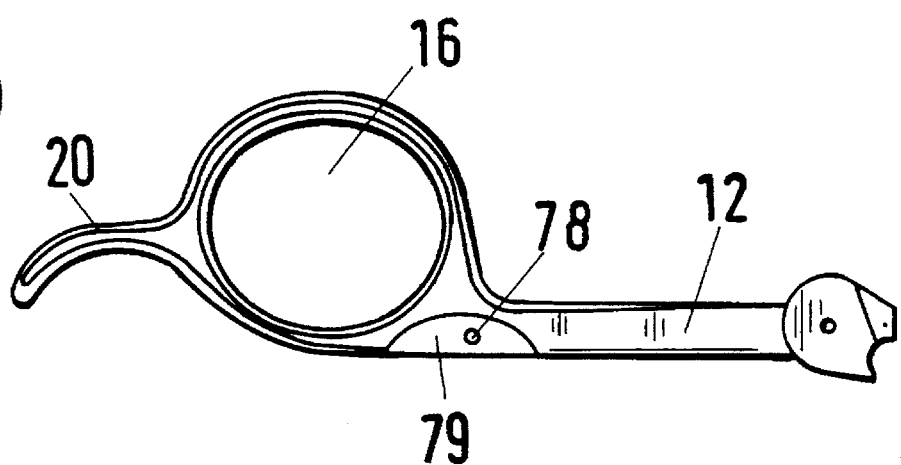
FIG. 10 is an elevational view of a second limb of FIG. 8.

FIG. 10 shows the position of the point 78 of articulation at the limb 12. A recess 79 having an approximately semi-oval cross section into which the point 76 of articulation is placed is provided in the proximity of the lug 16 at that side facing toward the second limb 14.

Figure 11:
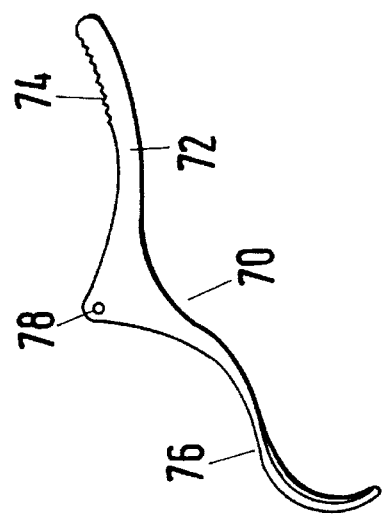
FIG. 11 is an elevational view of the locking device.

FIG. 11 shows the lock mechanism 70. It is broadened roughly triangularly in the transition region between the limb 72 and the actuation lever 76, whereby the point 78 of articulation lies at a free point of this triangle. The arm 72 carries the toothing 74 at an end section that covers approximately half through one-third of the length of the arm 72.

Figure 12:
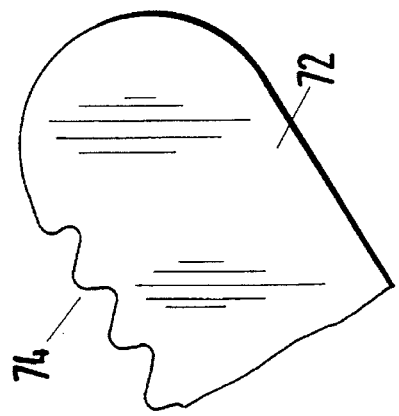
FIG. 12 is an enlarged elevational view of the end portion of the locking device.

FIG. 12 shows the end of the arm 72 with a part of the toothing 74. The teeth of the toothing have rounded-off points and steeply descending side walls at that side facing away from the rounded-off end of the arm 72 and have more flatly descending side walls at the side facing toward the rounded-off end of the arm 72.

Figure 13:
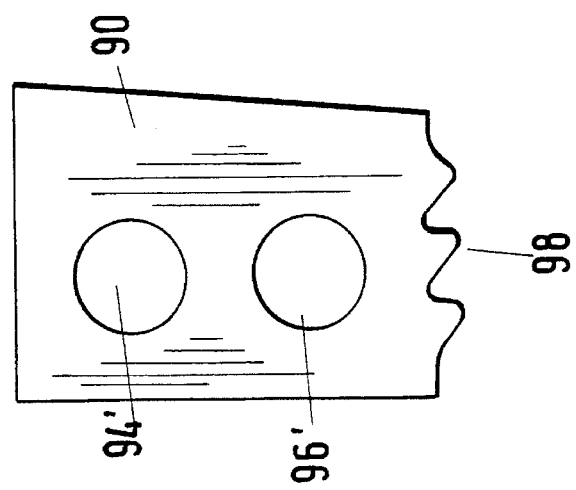
FIG. 13 is an enlarged elevational view of a ratchet means for a limb.

The ratchet means 90 in FIG. 13 is essentially cuboidally fashioned and carries a toothing 98 at one of its shorter sides, the shaping of this toothing 98 being matched to the toothing of the arm, so that a positive engagement derives between the two toothings. Bores 94', 96' are provided at locations which correspond to those of the bores 94, 96 of FIG. 8.

Figure 14:
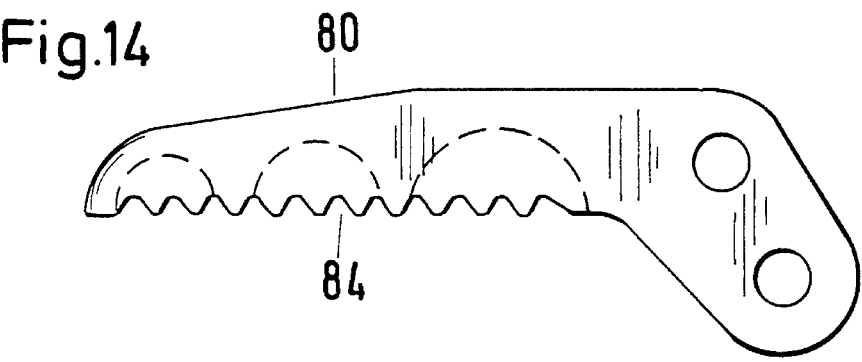
FIG. 14 is an enlarged elevational view of a gripping jaw of the gripping device of the instrument according to FIG. 8.
Figure 15:
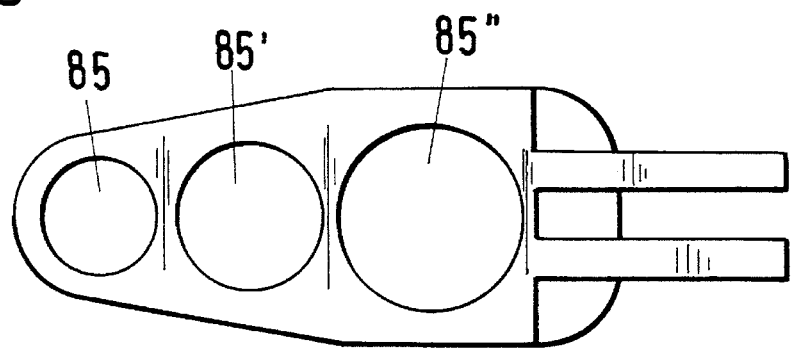
FIG. 15 is a bottom view of the gripping jaw of FIG. 14.

FIG. 14 shows a gripping jaw 80 of the gripping means that is secured to the instrument in the same way as the upper blade of FIG. 4. For gripping, a "blunt" toothing 84 is attached to the underside of the gripping jaw 80, whereby the toothing 84—as shown in FIG. 15—is fashioned in the successive, circular sections 85, 85', 85" with increasing diameters proceeding from the tip.

Figure 16:
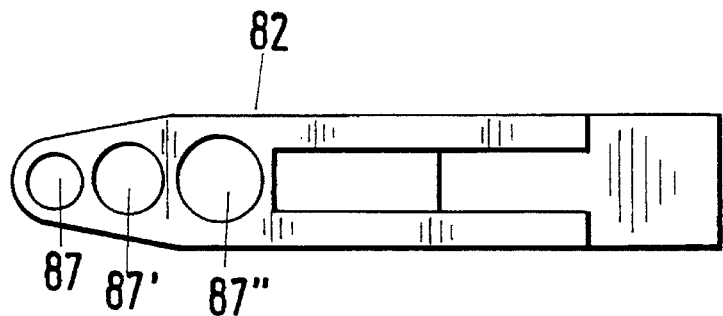
FIG. 16 is an enlarged top view of a second gripping jaw of the gripping device according to FIG. 8.
Figure 17:
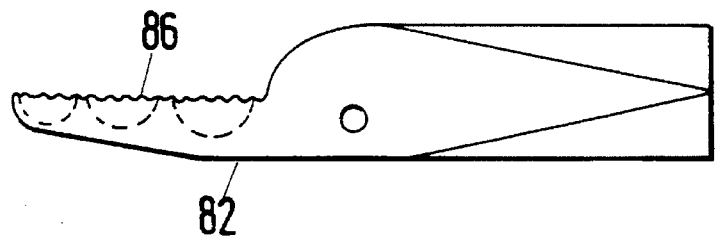
FIG. 17 is an elevational view of the gripping jaw of FIG. 16.

The cooperating member 82 of FIGS. 16 and 17 is corresponding fashioned, this having the toothing 86 fashioned in circular sections 87, 87', 87", again successively and with diameters that increase proceeding from the tip.

Both individually as well as in arbitrary combinations, the features of the invention disclosed in the above specification, in the drawing as well as in the claims can be critical for realizing the various embodiments of the invention.

I claim as my invention:

1. An instrument for endoscopic purposes, comprising:
   a first limb and a second limb, pivotable relative to one another around an axis and each of the limbs respectively having a lug for finger manipulation by a user;
   a transmission rod hingedly connected at a proximal end thereof to one of said limbs;
   two closable blades movable relative to one another between an open position and a closed position, one of said blades being hinged at a distal end of the transmission rod whereby the open position is achieved upon exertion of tension onto the transmission rod, and whereby the closed position is achieved upon exertion of a compression force onto the transmission rod;
   a bearing element rigidly connected to one of said limbs and pivotable around said axis, said transmission rod hingedly connected to said bearing element by a first pin; and
   wherein said bearing element comprises a recess and said respective other limb comprises a stop pin registered into said recess, said stop pin limiting the pivoting movement of said bearing element to limit maximum closure of said blades.

2. An instrument for endoscopic purposes, according to claim 1:
   wherein said bearing element is enclosed in a housing stationary with respect to the respective other of said limbs and said instrument comprises two disks of friction-reducing materials arranged on opposite sides of said bearing element within said housing.

3. The instrument according to claim 1, wherein said closable blades comprise a cutting device, and one of said closable blades is serrated.

4. The instrument according to claim 1, wherein said closable blades comprise a cutting device, and at least one of the blades comprises a plurality of arcuate, cutting sub-regions adjoining one another and offset from one another by cutting teeth.

5. The instrument according to claim 1 comprising an elongated tube mounted stationary with regard to one of said limbs and having a bush of friction reducing material therein, said transmission rod movable within said elongated tube and within said bush.

6. The instrument according to claim 1 comprising a lock mechanism arranged between said first limb and said second limb, for holding said first limb and said second limb in an adjustable relative angular position.

7. The instrument according to claim 6, wherein said locking mechanism comprises a first arm having a first end hinged to one of said limbs, and whose respective other end carries first a ratchet means that can be brought into engagement with a second, congruently fashioned ratchet means arranged at the respective other limb.

8. The instrument according to claim 7, wherein said first ratchet means comprises a series of teeth.

9. The instrument according to claim 7, wherein one of said limbs comprises a through opening into which the first ratchet means registers, and can be selectively conducted through.

10. The instrument according to claim 7, wherein said second ratchet means comprises a series of teeth.

11. The instrument according to claim 7, wherein said locking mechanism comprises an actuation lever for pivoting the arm around its point of articulation.

12. An instrument for endoscopic purposes, according to claim 4
wherein the closable blades comprise mating surfaces having blunt toothing and at least one essentially semispherical indent.

13. An instrument for endoscopic purposes comprising:
a first limb and a second limb, pivotable relative to one another around an axis and each of the limbs respectively having a lug for finger manipulation by a user;
a transmission rod hingedly connected at a proximal end thereof to one of said limbs;
two closable blades movable relative to one another between an open position and a closed position, one of said blades being hinged at a distal end of the transmission rod whereby the open position is achieved upon exertion of tension onto the transmission rod, and whereby the closed position is achieved upon exertion of a compression force onto the transmission rod and an open support shoulder plate for a finger of the user connected to one of the lugs respectively of said first limb, said support shoulder plate curved in the direction toward the second limb to allow pressing by a user's finger to open said first and second limbs, said support shoulder plate extending from said one lug to a free terminal end to allow free lateral access to the support shoulder plate by the user's finger, and
a lock mechanism arranged between said first limb and said second limb, for holding said first limb and said second limb in an adjustable relative angular position;
wherein said locking mechanism comprises a first arm having a first end hinged to one of said limbs, and whose respective other end carries a first ratchet means that can be brought into engagement with a second, congruently fashioned ratchet means arranged at the respective other limb, wherein said locking mechanism comprises an actuation lever for pivoting the arm around its point of articulation; and
wherein the actuation lever comprises a curvature that corresponds to the curvature of the support shoulder plate.

14. An instrument for endoscopic purposes, according to claim 13 wherein said bearing element is enclosed in a housing stationary with respect to the respective other of said limbs and said instrument comprises two disks of friction-reducing materials arranged on opposite sides of said bearing element within said housing.

15. The instrument according to claim 13 comprising an elongated tube mounted stationary with regard to one of said limbs and having a bush of friction reducing material therein, said transmission rod movable within said elongated tube and within said bush.

16. The instrument according to claim 13, wherein said first ratchet means comprises a series of teeth.

17. The instrument according to claim 13, wherein one of said limbs comprises a through opening into which the first ratchet means registers, and can be selectively conducted through.

18. The instrument according to claim 13, wherein said second ratchet means comprises a series of teeth.

19. An instrument for endoscopic purposes according to claim 13 wherein the closable blades comprise mating surfaces having blunt toothing and at least one essentially semispherical indent.

\* \* \* \* \*